United States Patent [19]
Zabotto et al.

[11] Patent Number: 5,439,672
[45] Date of Patent: Aug. 8, 1995

[54] COSMETIC COMPOSITION BASED ON AN AQUEOUS DISPERSION OF SMALL LIPID SPHERES

[75] Inventors: Arlette Zabotto, Paris; Jacqueline Griat, Ablon; Rose-Marie Handjani, Paris; Guy G. Vanlerberghe, Villevaude; Alian J. Ribier, Paris, all of France

[73] Assignee: L'Oreal, Paris, France

[21] Appl. No.: 155,591

[22] Filed: Nov. 18, 1993

Related U.S. Application Data

[63] Continuation-in-part of Ser. No. 480,135, Feb. 14, 1990, which is a continuation of Ser. No. 167,995, Mar. 14, 1988, abandoned, which is a continuation-in-part of Ser. No. 279,517, Jul. 1, 1981, abandoned.

[30] Foreign Application Priority Data

Jul. 1, 1980 [FR] France .................... 80 14657

[51] Int. Cl.$^6$ .............................................. A61K 7/42
[52] U.S. Cl. .................... 424/59; 252/309; 252/312
[58] Field of Search ............. 424/59; 252/309, 312

[56] References Cited

U.S. PATENT DOCUMENTS

| | | | |
|---|---|---|---|
| 3,957,971 | 5/1976 | Oleniacz | 424/70 |
| 4,217,344 | 8/1980 | Vanlerberghe | 424/60 |
| 4,309,448 | 1/1982 | Takaishi et al. | 424/70 |

FOREIGN PATENT DOCUMENTS

| | | | |
|---|---|---|---|
| 1617847 | 2/1971 | Germany | 424/70 |
| 2851369 | 6/1979 | Germany | 514/938 |
| 1539625 | 1/1979 | United Kingdom | 424/70 |
| 1539625 | 1/1979 | United Kingdom | 514/938 |

*Primary Examiner*—Bernard Dentz
*Assistant Examiner*—Zinna N. Davis
*Attorney, Agent, or Firm*—Cushman Darby & Cushman

[57] ABSTRACT

A cosmetic composition which is a stabilized, oil-in-water dispersion of spheres in an external aqueous phase. The spheres are organized molecular layers of a nonionic amphiphilic lipid material encapsulating an internal aqueous phase. The external aqueous phase, containing an oil, is free of any surface active emulsifying agent.

10 Claims, No Drawings

COSMETIC COMPOSITION BASED ON AN AQUEOUS DISPERSION OF SMALL LIPID SPHERES

This application is a continuation-in-part of application Ser. No. 07/480,135, filed on Feb. 14, 1990 which is a continuation of application Ser. No. 07/167,995 filed Mar. 14, 1988, now abandoned, which is a continuation-in-part of application Ser. No. 06/279,517, filed July 1, 1981, now abandoned.

BACKGROUND OF THE INVENTION

The present invention relates to a cosmetic composition consisting of a dispersion of small lipid spheres. Aqueous dispersions of this type have already been described in British Patent 1,539,625.

The small lipid spheres in these dispersions are in the form of roughly concentric laminae consisting of two or more lipid layers which are separated from one another by layers of an aqueous phase. They can thus be used to encapsulate water-soluble active substances, for example, pharmaceutical or cosmetic substances, in the aqueous compartments between the lipid layers, and to protect them from the exterior.

The above mentioned British patent also describes a new process for the preparation of an aqueous dispersion of small lipid spheres, which consists firstly in bringing the lipids which are to constitute the concentric laminae of the small spheres into contact with the aqueous solution to be encapsulated, the lipophilic/hydrophilic ratio of the chosen lipids being such that the latter swell in water or in the aqueous phase to be encapsulated, in order to form a plane lamellar phase; secondly in adding, to the lamellar phase, an aqueous solution which is to constitute the continuous external phase of the dispersion; and thirdly in subjecting the whole to vigorous agitation order to obtain a dispersion of small spheres, between the concentric laminae of which the aqueous phase to be encapsulated is trapped.

In order to form the concentric laminae of the small spheres, it is possible, according to the teaching of this British patent, to use either ionic or nonionic amphiphilic lipids. The following are preferred amongst the nonionic amphiphilic lipids:

a straight or branched-chain polyglycerol ether of the formula:

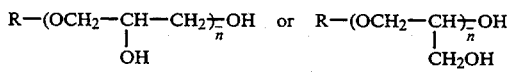

wherein
$\overline{n}$ has a statistical mean value of from 1 to 6 and
R is a straight or branched-chain saturated or unsaturated, aliphatic group containing 12 to 30 carbon atoms, a hydrocarbon group of a lanolin alcohol or a 2-hydroxyalkyl residue of a long-chain α-diol,
a straight or branched chain polyglycerol ether containing two fatty chains;
a polyglycerol ester of a straight chain fatty acid;
a polyoxyethylenated fatty alcohol;
a polyoxyethylenated sterol;
an ether of a polyhydric alcohol;
an ester of a polyhydric alcohol which can optionally be oxyethylenated;
a glycolipid of natural or synthetic origin;
a hydroxyamide of the formula

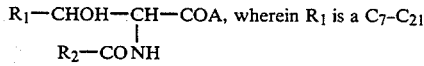

alkyl or alkenyl group, $R_2$ is a saturated or unsaturated $C_7-C_{31}$ hydrocarbon group, and

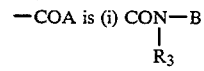

wherein B is a group derived from a mono- or polyhydroxylated primary or secondary amine and $R_3$ is hydrogen, methyl, ethyl or hydroxyethyl, or (ii) —COOZ wherein Z is a residue of a $C_3-C_7$ polyhydric alcohol.

Amongst the cosmetic active substance which can be encapsulated in the small lipid spheres, the above-mentioned British patent gives as examples substances for skin care, such as humectants, artificial tanning agents, skin-coloring agents, water soluble sun filters, antiperspirants, deodorants, astringents, freshening-up products, tonics, cicatrising agents, keratolytic agents, depilatories, perfumed waters and extracts from animal or plant tissues.

It has been observed that the cosmetic compositions referred to above, in the form of an aqueous dispersion of small lipid spheres, exhibit the advantage, compared with conventional preparations in the form of an of and water emulsion, of having a less aggressive action and consequently of causing less irritation when they are applied to the skin.

The aim of the present invention is to provide a cosmetic composition based on an aqueous dispersion of small lipid spheres, which makes it possible to combine the advantages of the dispersions of small spheres with the advantages resulting from the presence of cosmetic oils.

The present invention thus provides a cosmetic composition consisting of an aqueous dispersion of small spheres composed of organized molecular layers between which an internal aqueous phase is encapsulated, these layers consisting of at least one nonionic amphiphilic lipid, in which at least one oil is dispersed in the external aqueous phase which surrounds the small spheres, the said oil comprising fatty acid total esters of polyols, especially liquid triglycerides, and fatty acid esters of branched alcohols, of the formula R—COOR', in which formula R represents the radical of a higher fatty acid, which fatty acid contains from 8 to 20 carbon atoms and R' represents a branched hydrocarbon chain containing from 3 to 20 carbon atoms.

It has been observed, unexpectedly, that the small spheres of nonionic amphiphilic substances make it possible to stabilize the oil-in-water dispersion without requiring the addition of a surface active emulsifying agent and without causing the destruction of the small spheres. It is known from Harry's Cosmeticology, 6th Edition Vol. I, page 703, that surface active agents provide the majority of the emulsifying agents used in cosmetic emulsions; the stability of the emulsifying agents depends mainly on the presence of such emulsifiers having hydrophobic and hydrophilic moieties, the molecules of which are adsorbed onto the surface of the oil droplets to form a kind of continuous membrane which prevents direct contact between two adjacent droplets, for example, during shock. Thus in the present case, those skilled in the art might have expected that the nonionic amphiphilic lipids in the small spheres would act as an emulsifier by being adsorbed onto the surface of the oil droplets, but they would also have expected that this stabilization effect would also have the effect of causing the destruction of the concentric laminae of the small spheres. This has been found not to be the case at all and, surprisingly, the small spheres of nonionic amphiphilic substances of the invention are capable of stabilizing a dispersion of at least one vegetable oil, defined above, in an external aqueous phase by dispersing around the oil droplets while retaining their integrity.

As known from Harry's Cosmeticology, referenced above, at pages 701 and 702, hydrocolloids, i.e. substances yielding gel with water, such as plant gums and gelling polymers, are inefficient as primary emulsifier, although they are very useful as secondary stabilizers in oil-in-water lotions and semi-solid creams. They generally function merely through thickening the aqueous phase but have been reported to concentrate at the interface to form interfacial films.

U.S. Pat. No. 3,957,971 describes dispersions of small spheres of ionic amphiphilic substances or liposomes, which are used in cosmetic creams or lotions, that is to say, in water-in-oil or oil-in-water emulsions. In the present invention, the small spheres are composed not of ionic amphiphilic substances, but of nonionic amphiphilic substances. Moreover, it can be shown that the liposomes do not make it possible to stabilize a dispersion, in water, of a vegetable oil as defined above, whereas, totally unexpectedly, the small spheres of nonionic amphiphilic substances of the invention do make it possible to stabilize a dispersion of this type.

The cosmetic composition according to the invention can be prepared in two or more stages; in a first stage, an aqueous dispersion of small spheres is prepared from nonionic amphiphilic lipids using either the process described in British Patent 1,539,625 or the procedures described in French Patent 2,221,122, the disclosures of which are hereby incorporated by reference. In a second stage, once the aqueous dispersion of small spheres has been produced, the oil is added thereto. The oil is then dispersed in the external aqueous phase by agitation.

Preferably, the cosmetic composition according to the invention contains from 2 to 10% or even from 0.5 to 20% of nonionic amphiphilic lipid(s) which form the walls of the small spheres, and from 2 to 40% or even from 0.5 to 40% of dispersed , oil ( s ), these percentages being expressed by weight, relative to the total weight of the composition. Advantageously, the ratio by weight of nonionic amphiphilic lipid ( s ), relative to the dispersed oil (or oils), is from 0.2:1 to 1:1 or even from 1:40 to 40:1.

The oils which are incorporated into the composition according to the invention are fatty acid total esters of polyols, in particular liquid triglycerides, and fatty acid esters of branched alcohols, of the formula: R-COOR' in which formula R represents the radical of a higher fatty acid, which fatty acid contains from 8 to 20 carbon atoms and R' represents a branched hydrocarbon chain containing from 3 to 20 carbon atoms. Suitable fatty acid total esters of polyols include sunflower oil, corn oil, soya oil, gourd oil, grapeseed oil, and glycerol tricaprocaprylate. Purcellin oil may be mentioned specifically as a higher fatty acid ester of a branched alcohol.

Other vegetable oils usefully employed in the present invention include cocoa butter oil, dog-rose oil, black currant oil, Ximenia Americana oil, Pentacletra Macrophyla oil, Voandzeia oil, black currant obtusifolia oil, Trichilia. Emetica oil, Pongamia Glabra oil, passionflower oil, tomato seed oil, macadamia oil, sesame oil and jojoba oil.

The cosmetically active substance of the composition according to the present invention can be encapsulated inside or outside the small spheres. Thus, in a preferred embodiment, the oily phase of the composition contains one or more liposoluble cosmetic substances. In the preparation of the composition according to the invention, these substances are dissolved beforehand in the oil which is to be added to the dispersion of small lipid spheres. Representative liposoluble active cosmetic substances include, in particular, anti-sunburn filters such as 2-ethylhexyl para-dimethylaminobenzoate, or substances for improving the condition of dry or old skin, in particular, unsaponifiable substances such as those derived from soya and from avocado, tocopherols, vitamins E and F and antioxidants.

The oil-in-water dispersion which constitutes the external medium of the dispersion of small spheres can contain at least one additive, in particular a gelling agent or perfume. The additive can be added to the dispersion at the same time as the oil. The gelling agent can be introduced at a concentration of, say 0.1 to 2%, these percentages being expressed by weight, relative to the total weight of the composition. Amongst the gelling agents which can be used, there may be mentioned cellulose derivatives such as hydroxyethylcellulose, synthetic polymers, algae derivatives such as satiagum, and natural gums such as tragacanth. Hydroxyethylcellulose, a mixture of carboxyvinylic acids commercially available under the name "CARBOPOL 940", satiagum and tragacanth are preferably used as gelling agents.

The nonionic amphiphilic lipids which are to constitute the concentric laminae of the small spheres in the cosmetic composition according to the invention are typically:

straight or branched chain polyglycerol ethers having the following formulae:

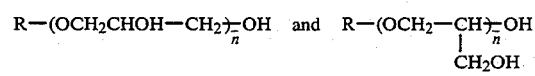

wherein $\overline{n}$ is a statistical average value from 2 to 6 and R represents a straight or branched saturated aliphatic chain containing from 16 to 20 carbon atoms or the hydrocarbon radical of a lanolin alcohol;

straight or branched polyglycerol ethers containing two fatty chains;

polyglycerol esters of a straight chain fatty acid; and polyoxyethylenated sterols.

At the moment of formation of the plane lamellar phase obtained by bringing the nonionic amphiphilic lipids into contact with the aqueous phase to be encapsulated, various auxiliary agents can be associated with the said lipids in order to modify, for example, the permeability or the surface charge of the small spheres. For this purpose, there may be mentioned the optional addition of long-chain alcohols and diols, sterols, in particular cholesterol and β-sitosterol, long-chain amines and their quaternary ammonium derivatives, in particular didodecyldimethylammonium bromide, hydroxyalkylamines, polyoxyethylenated fatty amines, long-chain aminoalcohol esters. and their salts and quaternary ammonium derivatives, phosphoric acid esters of fatty alcohols, in particular dicetyl phosphate, alkyl-sulphates, for example sodium cetyl-sulphate, and certain polymers such as polypeptides and proteins.

Apart from the auxiliary agents listed above, it is possible to add a preservative such as methyl parahydroxybenzoate.

The aqueous phase, whether internal or external, can contain a water-soluble cosmetic substance normally used for the care of the face, the hands or the body. Amongst these substances, there may be mentioned humectants such a glycerol, sorbitol, pentaerythritol, inositol and pyrrolidonecarboxylic acid and its salts, artificial tanning agents such as dihydroxyacetone, erythrulose, glyceraldehyde and γ-dialdehydes such as tartaraldehyde, skin-coloring agents, sun filters, antiperspirants, deodorants, astringents, freshening-up products, tonics, cicatrising agents, keratolytic agents, depilatories, perfumed waters, extracts from animal or plant tissues, such as proteins, amniotic liquid and polysaccharides, and antiseborrheic agents.

The following Examples further illustrate the present invention.

The cosmetic formulations given in the Examples below can be prepared in two or even three stages. In a first stage, an aqueous dispersion is produced in accordance with the process described in British Patent 1,539,625. The aqueous dispersion of small lipid spheres is prepared from:

a nonionic amphiphilic lipid;

sterols such as cholesterol or β-sitosterol;

optionally, dicetyl phosphate;

optionally, active cosmetic substances of a water soluble nature; and demineralized water which can contain a preservative.

In a second stage, oil is added and dispersed by intense mechanical agitation at ambient temperature and preferably at a temperature of about 40° C. It is during this second stage that liposoluble cosmetic substances, perfumes and/or gelling agents can optionally be incorporated, or if desired they can be added in a third stage.

EXAMPLE 1

Experiments for comparing a cosmetic composition according to the invention with a cosmetic composition of a known type.

Two compositions (A) and (B) are prepared; they are strictly identical, the only difference being that the preparation of composition (B) does not comprise a second stage for the addition of oil.

Composition (A) contains the following ingredients:

1st Stage:

| Nonionic amphiphilic lipid of the formula: | |
| --- | --- |
| 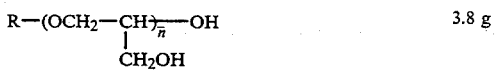 | 3.8 g |
| in which R is a hexadecyl radical and $\bar{n}$ has an average statistical value of 3 | |
| β-Sitosterol | 3.8 g |
| Dicetyl phosphate | 0.4 g |
| Methyl para-hydroxybenzoate | 0.3 g |
| Demineralized water | 66.7 g |

2nd Stage 25 g of sunflower oil are added to the above dispersion; the whole is subjected to mechanical agitation in order to obtain the final dispersion.

Cosmetic composition (B) is prepared in the same manner, but without a second stage for the addition of sunflower oil, the 25 g of oil being replaced in this case by an identical amount of demineralized water.

Cosmetic composition (A) consequently differs from cosmetic composition (B) in that it contains 25% of sunflower oil.

1) Measurements of the coefficient of friction of the skin during the spreading of cosmetic compositions (A) and (B).

The coefficient of friction of the skin during the spreading of cosmetic composition (A) or (B) is measured on the forearm of a subject with the aid of sensor driven with a rotational movement; the change in the opposing couple in the region of the sensor, during its rotation about itself, is recorded; the sensor is applied with a constant force (20 or 50 g).

The following results are obtained.

| | Variation in the coefficient of friction of the skin, measured 15 minutes after application | |
| --- | --- | --- |
| | Under a force of 20 g | Under a force of 50 g |
| Composition (B) | +209 | +245 |
| Composition (A) according to the invention (containing 25% of sunflower oil) | −40 | −60 |

It is observed that composition (B), that is to say the aqueous dispersion of small lipid spheres which does not contain oil, substantially increases the coefficient of friction of the skin, whereas composition (A) according to the invention, that is to say a dispersion of small spheres which does contain oil, produces the opposite effect. This significant lowering of the coefficient of friction of the skin results, in cosmetic terms, in the softness effect provided by formulation (A) according to the invention.

2) Measurement of the modulus of elasticity of human stratum corneum, carried out in vitro before and after application of cosmetic compositions (A) and (B) above These measurements were carried out on a laboratory apparatus for measuring the modulus of elasticity of the skin. A laboratory apparatus of this type is described in British Specification No. 2029018.

The experimental conditions are as follows:

Relative Humidity: 72% ±2

Temperature: 30° C. ±0.2

Amount of Product Applied: 5 mg/cm$^2$

The following results are obtained:

| PRODUCTS TESTED | Average % reduction in the modulus of elasticity 1 hour 30 minutes after application |
| --- | --- |
| Composition (B) | 0 |
| Composition (A) according to the invention | +15 |

The above results show clearly the difference in suppleness of the cornea, according to whether the dispersion of small spheres without an oily phase or a dispersion of small spheres with an oily phase is applied thereto.

EXAMPLE 2: Body-care Fluid.

1st Stage

As indicated above, an aqueous dispersion of small lipid spheres is produced from the following substances:

| | |
|---|---|
| Nonionic amphiphilic lipid of the general formula | |
| $R-(OCH_2-CH)_{\overline{n}}-OH$ <br> $\quad\quad\quad\quad\quad\; \mid$ <br> $\quad\quad\quad\quad\quad CH_2OH$ | 4.5 g |
| in which R is a hexadecyl radical and $\overline{n}$ has an average statistical value of 3 | |
| β-Sitosterol | 4.5 g |
| Dicetyl phosphate | 1.0 g |
| Methyl para-hydroxybenzoate | 0.3 g |
| Sodium salt of pyrrolidonecarboxylic acid | 2.0 g |
| Demineralized water | 56.5 g |

2nd stage: The following substances are added to the dispersion of small spheres obtained in the 1st stage:

| | |
|---|---|
| Perfume | 0.4 g |
| Sunflower Oil | 10.0 g |
| Mixture of carboxyvinylic acids marketed under the name "CARBOPOL 940" | 0.4 g |
| Triethanolamine | 0.4 g |
| Demineralized water | 20.0 g |

EXAMPLE 3: Face-care fluid

1st Stage

As indicated above, an aqueous dispersion of small lipid spheres is produced from the following substances:

| | |
|---|---|
| Nonionic amphiphilic lipid of the general formula | |
| $R-(OCH_2-CH)_{\overline{n}}-OH$ <br> $\quad\quad\quad\quad\quad\; \mid$ <br> $\quad\quad\quad\quad\quad CH_2OH$ | 6.0 g |
| in which R is a hexadecyl radical and $\overline{n}$ has a value of 2 | |
| Cholesterol | 1.6 g |
| Dicetyl phosphate | 0.4 g |
| Methyl para-hydroxybenzoate | 0.3 g |
| Demineralized water | 61.1 g |

2nd Stage

The following substances are added to the dispersion of small spheres obtained in the 1st stage:

| | |
|---|---|
| Perfume | 0.2 g |
| Grapeseed oil | 20.0 g |
| Mixture of carboxyvinylic acids marketed under the name "CARBOPOL 940" | 0.2 g |
| Triethanolamine | 0.2 g |
| Demineralized water | 10.0 g |

EXAMPLE 4: Hand-care Fluid 1st Stage

As indicated above, an aqueous dispersion of small lipid spheres is produced from the following substances:

| | |
|---|---|
| Polyoxyethylenated phytosterols (statistical average value of 5 for the oxyethylene units) | 6.0 g |
| Cholesterol | 2.0 g |
| Methyl para-hydroxybenzoate | 0.3 g |
| Demineralized water | 45.7 g |

2nd Stage

The following substances are added to the dispersion of small spheres obtained in the 1st stage:

| | |
|---|---|
| Perfume | 0.2 g |
| Jojoba oil | 25.0 g |
| Mixture of carboxyvinylic acids marketed under the name "CARBOPOL 940" | 0.4 g |
| Triethanolamine | 0.4 g |
| Demineralized water | 20.0 g |

EXAMPLE 5: Body-care Fluid.

1st Stage

As indicated above, an aqueous dispersion of small lipid spheres is produced from the following substances:

| | |
|---|---|
| Nonionic amphiphilic lipid of the general formula | |
| $R-(OCH_2-CH)_{\overline{n}}-OH$ <br> $\quad\quad\quad\quad\quad\; \mid$ <br> $\quad\quad\quad\quad\quad CH_2OH$ | 4.0 g |
| in which R is a hexadecyl radical and $\overline{n}$ has an average statistical value of 3 | |
| Cholesterol | 4.0 g |
| Methyl para-hydroxybenzoate | 0.3 g |
| Demineralized water | 45.5 g |

2nd Stage

The following substances are added to the dispersion of small spheres obtained in the 1st stage:

| | |
|---|---|
| Perfume | 0.4 g |
| Corn oil | 25.0 g |
| Mixture of carboxyvinylic acids marketed under the name "CARBOPOL 940" | 0.4 g |
| Triethanolamine | 0.4 g |
| Deminerlaized water | 20.0 g |

EXAMPLE 6: Face-care Fluid

1st stage

As indicated above, an aqueous dispersion of small lipid spheres is produced from the following substances:

| | |
|---|---|
| Nonionic amphiphilic lipid of the general formula | |
| $R-(OCH_2-CH)_{\overline{n}}-OH$ <br> $\quad\quad\quad\quad\quad\; \mid$ <br> $\quad\quad\quad\quad\quad CH_2OH$ | 0.95 g | in which R is a hexadecyl radical and $\bar{n}$
has an average statistical value of 3

| | |
|---|---|
| β-Sitosterol | 0.95 g |
| Dicetyl phosphate | 0.10 g |
| Methyl para-hydroxybenzoate | 0.30 g |
| Demineralized water | 64.80 g |

2nd Stage

The following substances are added to the dispersion of small spheres obtained in the 1st stage:

| | |
|---|---|
| Perfume | 0.4 g |
| Soya oil | 10.0 g |
| Unsaponifiable substances derived from soya | 2.0 g |
| Hydroxyethylcellulose marketed under the name "Natrosol 250 HHR" | 0.5 g |
| Demineralized water | 20.0 g |

EXAMPLE 7: Anti-sunburn Fluid.

1st Stage

As indicated above, an aqueous dispersion of small lipid spheres is produced from the following substances:

| | |
|---|---|
| Nonionic amphiphilic lipid of the general formula | |
|  | 3.6 g |
| in which R is a hexadecyl radical and $\bar{n}$ has an average statistical value of 3 | |
| β-Sitosterol | 3.6 g |
| Didodecyldimethylammonium bromide | 0.8 g |
| Methyl para-hydroxybenzoate | 0.3 g |
| Demineralized water | 45.9 g |

2nd Stage

The following substances are added to the dispersion of small spheres obtained in the 1st stage:

| | |
|---|---|
| Perfume | 0.4 g |
| Gourd oil | 22.0 g |
| 2-Ethylhexyl para-dimethylaminobenzoate | 3.0 g |
| Gum tragacanth | 0.4 g |
| Demineralized water | 20.0 g |

EXAMPLE 8: Hand-care Fluid

1st stage

As indicated above, an aqueous dispersion of small lipid spheres is produced from the following substances:

| | |
|---|---|
| Nonionic amphiphilic lipid of the general formula | |
|  | 3.8 g |
| in which R is a hexadecyl radical and $\bar{n}$ has an average statistical value of 3 | |
| β-Sitosterol | 3.8 g |
| Dicetyl phosphate | 0.4 g |
| Methyl para-hydroxybenzoate | 0.3 g |
| Glycerol | 3.0 g |
| Demineralized water | 42.5 g |

2nd Stage

The following substances are added to the dispersion of small spheres obtained in the 1st stage:

| | |
|---|---|
| Perfume | 0.2 g |
| Purcellin oil | 25.0 g |
| Satiagum | 1.0 g |
| Demineralized water | 20.0 g |

EXAMPLE 9: Body-care Fluid

1st Stage

As indicated above, an aqueous dispersion of small lipid spheres is produced from the following substances:

| | |
|---|---|
| Nonionic amphiphilic lipid of the general formula | |
|  | 3.8 g |
| in which R is a hexadecyl radical and $\bar{n}$ has an average statistical value of 3 | |
| β-Sitosterol | 3.8 g |
| Dicetyl phosphate | 0.4 g |
| Methyl para-hydroxybenzoate | 0.3 g |
| Demineralized water | 60.5 g |

2nd Stage

The following substances are added to the dispersion of small spheres obtained in the 1st stage:

| | |
|---|---|
| Perfume | 0.4 g |
| Glycerol tricaprocaprylate | 10.0 g |
| Mixture of carboxyvinylic acids marketed under the name "CARBOPOL 940" | 0.4 g |
| Triethanolamine | 0.4 g |
| Demineralized water | 20.0 g |

EXAMPLE 10: Face-care Cream

1st Stage

As indicated above, an aqueous dispersion of small lipid spheres is produced from the following substances:

| | |
|---|---|
| Nonionic amphiphilic lipid of the general formula | |
| 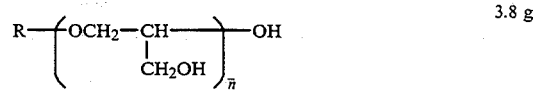 | 3.8 g |
| in which R is a hexadecyl radical and $\bar{n}$ has an average statistical value of 3 | |
| β-Sitosterol | 3.8 g |
| Dicetyl phosphate | 0.4 g |
| Preservative | 0.3 g |
| Demineralized water | 47.6 g |

2nd Stage

The following substances are added to the dispersion of small spheres obtained in the 1st stage:

| | |
|---|---|
| Sunflower oil | 35.0 g |
| Perfume | 0.6 g |
| Mixture of carboxyvinylic acids marketed under the name "CARBOPOL 940" | 0.2 g |
| Triethanolamine | 0.2 g |
| Demineralized water | 8.1 g |

EXAMPLE 11: Fluid Cream For the Care of Dry Skin

1st Phase

As indicated above, an aqueous dispersion of lipid spheres is produced from the following components:

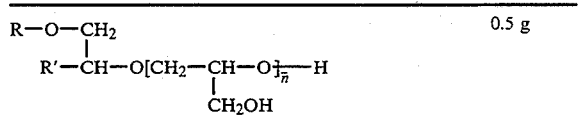

| | |
|---|---|
| wherein R = dodecyl, R' = equimolar mixture of tetradecyl and hexadecyl radicals, and $\bar{n}$ = average statistical value determined by NMR as being equal to 5.5 (included in French application 79-23253) | 7.6 g |
| Dimyristyl phosphate | 0.4 g |
| Methyl parahydroxybenzoate | 0.3 g |
| Demineralized water | 51.28 g |

2nd Phase

To the dispersion of spheres obtained in the above 1st stage, the following components are added:

| | |
|---|---|
| Macadamia oil | 25 g |
| Mixture of carboxyvinyl acids, sold under the trade name "CARBOPOL 940" by Goodrich | 0.4 g |
| Triethanolamine | 0.4 g |
| Demineralized water | 14.62 g |

EXAMPLE 12

Concentrate of Lipid Spheres For The Care of Exfoliated Skin

1st Phase

As indicated above, an aqueous dispersion of lipid spheres is produced from the following components:

| | |
|---|---|
| Nonionic amphiphilic lipid having the formula: 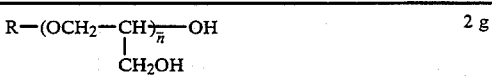 wherein R is hexadecyl and $\bar{n}$ has a statistical average value of 3 | 9.5 g |
| Cholesterol | 9.5 g |
| Dicetylphosphate | 1.0 g |
| Methyl parahydroxybenzoate | 0.3 g |
| Demineralized water | 79.2 g |

2nd Phase

To the dispersion of spheres produced in said 1st phase, there is added 0.5 g of black currant oil.

EXAMPLE 13: Body Milk.

1st phase

As indicated above, an aqueous dispersion of lipid spheres is produced from the following components:

| | |
|---|---|
| $\begin{array}{l} R-O-CH_2 \\ \phantom{R-O-}| \\ R'-CH-O[CH_2-CH-O]_{\bar{n}}-H \\ \phantom{R'-CH-O[CH_2-}| \\ \phantom{R'-CH-O[CH_2-}CH_2OH \end{array}$ wherein R = dodecyl, R' = equimolar mixture of tetradecyl and hexadecyl radicals, and $\bar{n}$ = average statistical value determined by NMR as being equal to 5.5 (included in French application 79-23253) | 0.5 g |
| Dimyristyl phosphate | 0.025 g |
| Methyl parahydroxybenzoate | 0.3 g |
| Demineralized water | 63.175 g |

2nd Phase

To the dispersion of spheres produced in said 1st phase, the following components are added:

| | |
|---|---|
| Sesame oil | 20 g |
| Mixture of carboxyvinyl acids, sold under the trade name "CARBOPOL 940" by Goodrich | 0.4 g |
| Triethanolamine | 0.4 g |
| Demineralized water | 15.2 g |

EXAMPLE 14: Fluid for the Care of the Skin

1st Stage

As indicated above, an aqueous dispersion of lipid spheres is produced from the following components:

| | |
|---|---|
| $\begin{array}{l} R-(OCH_2-CH)_{\bar{n}}-OH \\ \phantom{R-(OCH_2-}| \\ \phantom{R-(OCH_2-}CH_2OH \end{array}$ wherein R = hexadecyl and $\bar{n}$ = statistical average value determined by NMR as being equal to 3 | 2 g |
| Cholesterol | 2 g |
| Dicetyl phosphate | 0.2 g |
| Glycerol | 5 g |
| Demineralized water | 14.2 g |

2nd Phase

To the dispersion of spheres obtained in said 1st phase, the following components are added:

| | |
|---|---|
| Cocoa butter oil | 5 g |
| Dog-rose oil | 5 g |
| Perfume | 0.5 g |

13

Third Phase

There are added to the resulting mixture of the 1st and 2nd phases, the following components:

| | |
|---|---|
| Mixture of carboxyvinylic acids, sold under the trade name "CARBOPOL 940" by Goodrich | 0.2 g |
| Triethanolamine | 0.2 g |
| Propyl parahydroxybenzoate | 0.3 g |
| Propyl parahydroxybenzoate | 0.3 g |
| Demineralized water | 65.4 g |

EXAMPLE 15: Cream For the Care of the Skin

1st Phase

As indicated above, an aqueous dispersion of lipid spheres is produced from the following components:

| | |
|---|---|
| Nonionic amphiphilic lipid having the formula: $$R-(OCH_2-CH)_{\overline{n}}-OH$$ $$\quad\quad\quad\quad\quad\; | \quad\quad$$ $$\quad\quad\quad\quad\quad CH_2OH$$ wherein R = hexadecyl and $\overline{n}$ = statistical average value determined by NMR as being equal to 3 | 4.5 g |
| Cholesterol | 4.5 g |
| Dicetyl phosphate | 0.5 g |
| Demineralized water | 38 g |

2nd Phase

To the dispersion of spheres obtained in said 1st phase, the following components are added:

| | |
|---|---|
| Macadamia oil | 10 g |
| Black currant oil | 5 g |
| White petrolatum, Codex | 5 g |
| Propyl parahydroxybenzoate | 0.1 g |
| Perfume | 0.3 g |

Third Phase

There are added to the resulting mixture of the 1st and 2nd phases, the following components:

| | |
|---|---|
| Mixture of carboxyvinylic acids, sold under the trade name "CARBOPOL 940" by Goodrich | 0.4 g |
| Triethanolamine | 0.4 g |
| Methyl parahydroxybenzoate | 0.2 g |
| Demineralized water | 31.1 g |

EXAMPLE 16: Cream For the Care of the Face

1st Stage

As indicated above, an aqueous dispersion of lipid spheres is produced from the following components:

| | |
|---|---|
| Nonionic amphiphilic lipid having the commercial name "Plurol stearique WL 1009" sold by the firm Gattefosse (defined as Polyglyceryl 6 distearate (CTFA name) | 3.8 g |
| Cholesterol | 3.8 g |
| Dicetyl phosphate | 0.4 g |
| Methyl para-hydroxybenzoate | 0.3 g |

| | |
|---|---|
| Demineralized water | 51.28 g |

2nd Stage

To the dispersion of spheres obtained in said 1st phase, the following components are added:

| | |
|---|---|
| Macadamia oil | 25.0 g |
| Mixture of carboxyvinylic acids, sold under the trade name "CARBOPOL 940" by GOODRICH | 0.4 g |
| Triethanolamine | 0.4 g |
| Demineralized water | 14.62 g |

We claim:

1. A composition suitable for use in cosmetics consisting essentially of an oil-in-water dispersion wherein the external water phase of said dispersion contains an oil dispersed therein, said oil-in-water dispersion being stabilized by spheres dispersed in said external water phase without causing destruction of said spheres, said spheres consisting essentially of organized molecular layers of a nonionic amphiphilic lipid material encapsulating an internal aqueous phase, said nonionic amphiphilic lipid material being selected from the group consisting of
   (i) a straight or branched chain polyglycerol ether having the following formulae:

$$R-(OCH_2CHOHCH_2)_{\overline{n}}-OH \quad \text{and} \quad R-(OCH_2-CH)_{\overline{n}}-OH$$
$$\quad\quad\quad\quad\quad\quad\quad\quad\quad\quad\quad\quad\quad\quad\quad\quad\quad\quad\quad\quad\quad | $$
$$\quad\quad\quad\quad\quad\quad\quad\quad\quad\quad\quad\quad\quad\quad\quad\quad\quad\quad\quad\; CH_2OH$$

wherein $\overline{n}$ has a statistical average value from 2 to 6 and R represents a straight or branched chain saturated aliphatic group containing from 16 to 20 carbon atoms or a hydrocarbon group of a lanolin alcohol, and
   (ii) a polyoxyethylenated sterol;
said oil contained in said external water phase being selected from the group consisting of (a) a fatty acid total ester of a polyol, (b) a fatty acid ester of a branched alcohol and having the formula R-COOR' wherein R represents the radical of a fatty acid containing 8 to 20 carbon atoms and R' represents a branched hydrocarbon chain containing 3 to 20 carbon atoms, and (c) jojoba oil.

2. The composition of claim 1 wherein said nonionic amphiphilic lipid material is a polyglycerol ether in the formulae of which R is a chain containing 16 carbon atoms and $\overline{n}=3$.

3. The composition of claim 1 wherein said oil is selected from the group consisting of sunflower oil, corn oil, soya oil, gourd oil, grape seed oil and glycerol tricaprocaprylate.

4. The composition of claim 1 wherein said oil is purcellin oil.

5. The composition of claim 1 wherein said nonionic amphiphilic lipid material is present in an amount ranging from 2 to 10 weight percent of said composition and said oil is present in an amount ranging from 2 to 40 weight percent of said composition, the weight ratio of said lipid material to said oil ranging from 0.2:1 to 1:1.

6. The composition of claim 1 wherein the oil is soya oil and the nonionic amphiphilic lipid material is present in an amount of 0.95 weight percent of said composition, said oil being present in an amount of 10 weight percent of said composition.

7. The composition of claim 1 wherein said external aqueous phase also contains a gelling agent present in an amount of 0.1 to 2 percent by weight based on the total weight of said composition.

8. The composition of claim 7 wherein said gelling agent is hydroxyethylcellulose, satia gum or tragacanth gum.

9. The composition of claim 1 wherein said nonionic amphiphilic lipid material is admixed with at least one of cholesterol, β-sitosterol or dicetyl phosphate.

10. A composition suitable for use in cosmetics consisting essentially of a dispersion of spheres in an external aqueous phase containing an oil so as to provide a stabilized, oil-in-water dispersion without the addition of an emulsifying agent, said spheres consisting essentially of organized molecular layers of a nonionic lipid material encapsulating an internal aqueous phase, said nonionic lipid material being selected from the group consisting of (i) a straight or branched chain polyglycerol ether having the following formulae:

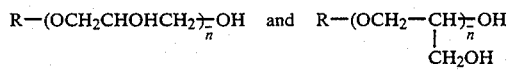

wherein $\bar{n}$ has a statistical average value from 2 to 6 and R, in each, represents a straight or branched chain saturated aliphatic group containing from 16 to 20 carbon atoms or a hydrocarbon group of a lanolin alcohol, and (ii) a polyoxyethylenated sterol;

said nonionic lipid material being present in an amount from 2 to 10 weight percent based on the total weight of said composition, said oil contained in said external aqueous phase being selected from the group consisting of (a) a liquid triglyceride and (b) a fatty acid ester of a branched alcohol and having the formula R-COOR' wherein R represents the radical of a fatty acid, which fatty acid contains 8 to 20 carbon atoms and R' represents a branched hydrocarbon chain containing 3 to 20 carbon atoms, said oil being present in an amount ranging from 2 to 40 weight percent of said composition, the weight ratio of said lipid material to said oil ranging from 0.2:1 to 1:1.

* * * * *